United States Patent
Soulie et al.

(10) Patent No.: US 10,376,612 B2
(45) Date of Patent: Aug. 13, 2019

(54) PYROPHOSPHATE TYPE MATERIAL, PROCESS FOR PREPARING SUCH A MATERIAL AND USE FOR BONE REPAIR

(71) Applicants: INSTITUT NATIONAL POLYTECHNIQUE DE TOULOUSE, Toulouse (FR); CENTRE NATIONAL DE LA RECHERCHE SCIENTIFIQUE, Paris (FR); UNIVERSITE PAUL SABATIER TOULOUSE III, Toulouse (FR)

(72) Inventors: Jérémy Soulie, Toulouse (FR); Christèle Combes, Mervilla (FR); Christian Rey, Aureville (FR); Pierre Gras, Gravason (FR)

(73) Assignees: INSTITUT NATIONAL POLYTECHNIQUE DE TOULOUSE, Toulouse (FR); CENTRE NATIONAL DE LA RECHERCHE SCIENTIFIQUE, Paris (FR); UNIVERSITE PAUL SABATIER TOULOUSE III, Toulouse (FR)

( * ) Notice: Subject to any disclaimer, the term of this patent is extended or adjusted under 35 U.S.C. 154(b) by 0 days.

(21) Appl. No.: 15/515,598

(22) PCT Filed: Sep. 29, 2015

(86) PCT No.: PCT/FR2015/052584
§ 371 (c)(1),
(2) Date: Mar. 30, 2017

(87) PCT Pub. No.: WO2016/051063
PCT Pub. Date: Apr. 7, 2016

(65) Prior Publication Data
US 2017/0304493 A1    Oct. 26, 2017

(30) Foreign Application Priority Data

Sep. 30, 2014  (FR) ..................... 14 59245

(51) Int. Cl.
| | | |
|---|---|---|
| A61L 27/32 | (2006.01) | |
| C01B 25/40 | (2006.01) | |
| C01B 25/42 | (2006.01) | |
| C01B 25/45 | (2006.01) | |
| A61L 27/54 | (2006.01) | |
| A61L 27/56 | (2006.01) | |
| C01B 25/168 | (2006.01) | |
| C03C 1/00 | (2006.01) | |
| C03C 3/16 | (2006.01) | |
| C03C 4/00 | (2006.01) | |
| C03C 10/00 | (2006.01) | |

(52) U.S. Cl.
CPC ............. *A61L 27/32* (2013.01); *A61L 27/54* (2013.01); *A61L 27/56* (2013.01); *C01B 25/168* (2013.01); *C01B 25/40* (2013.01); *C01B 25/42* (2013.01); *C01B 25/425* (2013.01); *C01B 25/45* (2013.01); *C03C 1/006* (2013.01); *C03C 3/16* (2013.01); *C03C 4/0014* (2013.01); *C03C 10/00* (2013.01); *A61L 2300/112* (2013.01); *A61L 2300/412* (2013.01); *A61L 2420/02* (2013.01); *A61L 2430/02* (2013.01); *C01P 2002/72* (2013.01); *C01P 2002/82* (2013.01); *C01P 2002/86* (2013.01); *C01P 2002/88* (2013.01); *C01P 2004/02* (2013.01); *C01P 2004/03* (2013.01)

(58) Field of Classification Search
None
See application file for complete search history.

(56) References Cited

U.S. PATENT DOCUMENTS

2004/0175430 A1    9/2004    Berger et al.

FOREIGN PATENT DOCUMENTS

| EP | 1 413 322 A2 | 4/2004 |
|---|---|---|
| EP | 2 228 080 A1 | 9/2010 |
| WO | 01/54746 A2 | 8/2001 |

OTHER PUBLICATIONS

Christofferson et al. "Growth and precipitation of a monoclinic calcium pyrophosphate tetrahydrate indicating auto-inhibition at pH7", Journal of Crystal Growth 212, 500-506 (Year: 2000).*
Kannan et al., "Synthesis and structural characterization of strontium- and magnesium-co-substituted sz-tricalcium phosphate," Acta Biomaterialia, Aug. 11, 2009, pp. 571-576, vol. 6, No. 2, Elsevier, Amsterdam, NL.
Abbarin et al., Effect of potassium and magnesium doping on mechanical properties and in vitro degradation behavior of calcium polyphosphate, J. Mater. Sci., Oct. 6, 2012, pp. 1604-1613, vol. 48, No. 4, Kluwer Academic Publishers.

(Continued)

*Primary Examiner* — James W Rogers
(74) *Attorney, Agent, or Firm* — Im IP Law; C. Andrew Im; Chai Im

(57) ABSTRACT

A material, especially a glassy material of pyrophosphate type, corresponding to the general formula (I): $\{[(M^{2+})_{1-x}(R^{+})_{2x}]_2[(P_2O_7^{4-})_{1-y}(PO_4^{3-})_{4y/3}]\}$ n($H_2O$) in which x and y are positive rational numbers each between 0 and 0.8, and n is such that the weight percentage of water in the material is greater than 0 and less than or equal to 95. $M^{2+}$ represents a bivalent ion of a metal chosen from calcium, magnesium, strontium, copper, zinc, cobalt, manganese and nickel, or any mixture of such bivalent ions. $R^{+}$ represents a monovalent ion of a metal selected from potassium, lithium, sodium, and silver, or any mixture of such monovalent ions. This material in particular can be used in manufacturing of bone replacements or prosthesis coatings.

12 Claims, 4 Drawing Sheets

(56) References Cited

OTHER PUBLICATIONS

Berger et al., "Rapid resorbable, glassy crystalline materials on the basis of calcium alkali orthophosphates," Biomaterials, Aug. 2, 1985, pp. 1241-1248, Elsevier Science Limited, Great Britain.

Xie et al., "Application of K/Sr co-doped calcium polyphosphate bioceramic as scaffolds for bone substitutes," J. Mater. Sci: Mater. Med., Feb. 5, 2012, pp. 1033-1044, vol. 23, No. 4, Kluwer Academic Publishers.

Hench et al., "Bonding mechanisms at the interface of ceramic prosthetic materials," J. Biomed. Mater. Res., 1971, pp. 117-141, vol. 2.

Hench et al., "Direct chemical bond of bioactive glass-ceramic materials to bone and muscle," J. Biomed. Mater. Res., 1973, pp. 25-42, vol. 7.

Pemberton et al., "Raman spectroscopy of calcium phosphate glasses with varying calcium oxide modifier concentrations," Chem. Mater., 1991, pp. 195-200, vol. 3.

Kokubo et al., "Solutions able to reproduce in vivo surface-structure changes in bioactive glass-ceramic A-W," J. Biomed. Mater. Res., 1990, pp. 721-734, vol. 24.

Sepulveda et al., "In vitro dissolution of melt-derived 45S5 and sol-gel derived 58S bioactive glasses," J. Biomed. Mater. Res., 2002, pp. 301-311, vol. 61.

Parish et al., "Automated colorimetric assay for T cell cytotoxicity," J. Immun. Methods, 1983, pp. 225-237, vol. 58.

Okada et al., "Synthesis and modification of apatite nanoparticles for use in dental and medical applicaitons," Japanese Dental Science Review, 2015, pp. 85-95, vol. 51.

Soulie et al., "Development of a new family of monolithic calcium (pyro) phosphate glasses by soft chemistry," Acta Biomaterialia, May 21, 2016, pp. 320-327, vol. 41.

Kim et al., "Synthesis of Si, Mg substituted hydroxyapatites and their eintering behaviors," Biomaterials, 2003, pp. 1389-1398, vol. 24.

\* cited by examiner

PYROPHOSPHATE TYPE MATERIAL, PROCESS FOR PREPARING SUCH A MATERIAL AND USE FOR BONE REPAIR

RELATED APPLICATIONS

This application is a § 371 application from PCT/FR2015/052584 filed Sep. 29, 2015, which claims priority from French Patent Application No. 14 59245 filed Sep. 30, 2014, each of which is herein incorporated by reference in its entirety.

FIELD OF THE INVENTION

The present invention comes within the field of biomaterials used as bone substitutes, in particular belonging to the family of the so-called bioactive glasses. More specifically, the invention relates to a material of metal pyrophosphate type and also to a process for preparing such a material. The invention also relates to the use of this material for the purpose of bone repair and/or reconstruction.

BACKGROUND OF THE INVENTION

For the repair of a bone defect, it is important, in parallel with the installation of a replacement structure, to promote the reconstruction of bone tissue which will gradually colonize or take the place of the bone substitute.

To this end, specific materials, known as bioactive materials, having been developed by the prior art. When they are implanted in the body, these materials are capable of reacting chemically with the biological fluids, the product of the reaction being a hydroxyapatite which promotes the formation of the bone matrix and bone growth.

Such bioactive materials developed by the prior art are, for example, bioactive glasses of soda-lime phospho-silicate type, corresponding to the general formula $SiO_2$—$P_2O_5$—$CaO$—$Na_2O$. An example thereof is the glass sold under the name BIOGLASS®, with a molar composition: 55% $SiO_2$—20% CaO—20% $Na_2O$—5% $P_2O_5$ (Hench et al., 1971, *J. Biomed. Mater. Res.*, 2, 117-141; Hench et al., 1973, *J. Biomed. Mater. Res.*, 7, 25-42).

Such glasses are conventionally prepared by "fusion" techniques, providing a heat treatment at very high temperature, in order to obtain the vitreous material. They exhibit in particular the disadvantage of a relatively rapid surface dissolution in the body, of the order of a few hours. Glasses composed solely of phosphorus and calcium oxides have furthermore been developed (Pemberton et al., 1991, *Chem. Mater.*, 3, 195-200). These glasses are prepared solely by fusion and exhibit surface dissolution kinetics which are also very rapid, of only a few hours.

OBJECT AND SUMMARY OF THE INVENTION

The present invention aims at providing a bioactive material, that is to say a material capable of reacting in the human or animal body to promote the formation of the bone matrix, which exhibits a rate of dissolution in biological fluids which, on the one hand, is slower than the materials provided by the prior art and which, on the other hand, is controllable, so as to make possible, in the body in which this material is implanted, a modulation of the rate of its replacement by bone according to the targeted pathology.

The invention also aims that this material be devoid of any toxicity for human and animal bodies and that it be composed solely of constituents that are naturally present in these bodies.

An additional objective of the invention is for this material to exhibit a controlled morphology and controlled properties, while being relatively inexpensive to prepare.

It has been discovered by the present inventors that such objectives can be achieved by a material corresponding to a specific general formula, in which the phosphorus is present either solely in the form of pyrophosphate $P_2O_7^{4-}$ ions or in the form of a mixture composed solely of pyrophosphate $P_2O_7^{4-}$ ions and of orthophosphate $PO_4^{3-}$ ions. It has also been discovered by the present inventors that the modulation of the relative molar percentage between these phosphate forms makes it possible to modulate the rate of dissolution of the material in biological fluids.

Thus, there is provided, according to the present invention, a material corresponding to the general formula (I):

wherein:

x and y are positive rational numbers such that:

$0 \leq x \leq 0.8$ $0 \leq y \leq 0.8$ n is a positive rational number such that the percentage by weight of water in the material is greater than 0 and less than or equal to 95, $M^{2+}$ represents a divalent ion of a metal chosen from:

alkaline earth metals: calcium (Ca), magnesium (Mg), strontium (Sr), copper (Cu), zinc (Zn), cobalt (Co), manganese (Mn) and nickel (Ni), or any mixture of such divalent ions, for example a mixture of magnesium and calcium, and $R^+$ represents a monovalent ion of a metal chosen from:

alkali metals: potassium (K), lithium (Li) or sodium (Na); and silver (Ag), or any mixture of such monovalent ions, for example a mixture of sodium and potassium.

The material according to the invention in particular does not comprise an element, such as silicon, titanium or aluminum, liable to generate oxides which form the vitreous network, and the incorporation of which in the human body might prove to be harmful.

The phosphorus contained in the material according to the invention is in addition present therein solely in the form of pyrophosphate entities or in the form of a mixture of pyrophosphate entities and orthophosphate entities, that is to say in forms naturally present in the body. The material according to the invention in particular does not contain phosphates in the form of metaphosphate entities. The relative molar percentages of each of the phosphate forms can in addition vary, giving rise to rates of dissolution of the material in biological fluids which are also variable, this variation advantageously being controllable, and slower than those of the materials provided by the prior art. It has in particular been demonstrated by the present inventors that, whatever these relative molar percentages, the material according to the invention remains substantially stable in a model biological fluid for a period of time of greater than 7 days.

In specific embodiments of the invention, in the general formula (I), y is between 0 and 0.5, limits included, with the result that the percentage in moles of pyrophosphate entities, with respect to the total molar amount of phosphates, is between 50 and 100%. Such a characteristic advantageously confers, on the material according to the invention, an even slower rate of dissolution in biological fluids.

In particularly preferred embodiments of the invention, in the general formula (I), n is such that the percentage by weight of water in the material is greater than or equal to 5 and less than or equal to 95. Such a characteristic advantageously ensures that the material comprises an amorphous phase. This results in numerous advantages, in particular the possibility of having active molecules diffuse into the material, a better regulation of bioresorption, and so on.

The material according to the invention does not exhibit any cytotoxicity. In particular, cells of human origin remain viable and metabolically active after several days of culturing in vitro in the presence of a medium which has been in contact with this material for 24 hours.

In addition, it exhibits an effect of stimulation of bone mineralization in vivo.

The material according to the invention can exhibit different degrees of hydration and come under several different types of materials.

In particular, the material according to the invention can be a vitreous material, such as a glass or a glass-ceramic, particularly suited to use in bone repair and/or reconstruction, in particular in comparison with crystalline materials. In this case, in the general formula (I), n is such that the percentage by weight of water in the material is greater than 0 and less than or equal to 20, and preferably between 5 and 20, limits included.

In alternative forms of the invention, in the general formula (I), n is such that the percentage by weight of water in the material is greater than 20 and less than or equal to 95. The material then has the form of a gel. Such a gel proves especially particularly advantageous for the formation of bone substitutes in the form of soft pastes, for the repair of geometrically complex bone defects.

The material according to the invention can be such that the R/P molar ratio is less than or equal to 0.3. In the dry state, that is to say when, in the general formula (I), n is such that the percentage by weight of water in the material is less than or equal to 20%, preferably between 5 and 20%, it then constitutes a glass, that is to say an amorphous material.

Otherwise, the material according to the invention can be such that the R/P molar ratio is greater than 0.3. In the dry state, that is to say when, in the general formula (I), n is such that the percentage by weight of water in the material is less than or equal to 20%, preferably between 5 and 20%, it then constitutes a glass-ceramic, that is to say a material formed of a vitreous matrix in the amorphous state, in which crystals or nanocrystals are homogeneously dispersed.

Preferably, the material according to the invention comprises an amorphous phase representing at least 70% by weight of the weight of the material.

The material according to the invention can be shaped as a thin layer, in particular with a thickness of less than 10 μm, or as a thick layer, in particular with a thickness of greater than 10 μm. It can otherwise be provided, when it is in the vitreous form, the percentage by weight of water being less than or equal to 20% therein, in any form conventional in itself for vitreous materials, in particular the form of monoliths, that is to say of three-dimensional entities, the three dimensions of which are greater than a millimeter, or of powder of nanoparticles, more particularly with a size of between 1 and 500 nm, and/or of microparticles, more particularly with a size of between 500 nm and 1 mm. It can otherwise be shaped in the form of fibers.

In specific embodiments of the invention, particularly advantageous for biological applications, when $M^{2+}$ represents a mixture of divalent ions of metals chosen from calcium, magnesium, strontium, copper, zinc, cobalt, manganese and nickel, this mixture mainly contains calcium, preferably in a molar amount of greater than or equal to 90%, with respect to the total amount of ions in the $M^{2+}$ mixture.

When $R^+$ represents a mixture of monovalent ions of metals chosen from potassium, lithium, sodium and silver, this mixture mainly contains potassium and/or sodium, preferably in a molar amount of greater than or equal to 90%, with respect to the total amount of ions in the $R^+$ mixture.

The material according to the invention can advantageously have additional properties. These properties are in particular chosen according to the specific field of application for which the material is intended to be employed.

Thus, according to a specific characteristic of the invention, the material can be doped with an additional element exhibiting one or more properties which are advantageous for the targeted application.

The material according to the invention can thus comprise a percentage by weight of between 0 and 15%, limits included, preferably of less than or equal to 10%, of an element chosen from copper (Cu), iron (Fe), chromium (Cr), manganese (Mn), zinc (Zn), silver (Ag), lanthanum (La), lithium (Li), cerium (Ce), praseodymium (Pr), promethium (Pm), samarium (Sm), europium (Eu), gadolinium (Gd), terbium (Tb), dysprosium (Dy), erbium (Er), thulium (Tm), neodymium (Nd) and ytterbium (Yb), or of any mixture of such elements. Such an element or mixture of elements will be denoted in the present description by the term doping agent.

In particular, for biological applications, the material according to the invention can meet one, preferably several, and even all, of the characteristics below:
  $M^{2+}$ represents a divalent ion of a metal chosen from calcium, magnesium and strontium, or a mixture of such ions, the calcium ion then preferably representing at least 90%, in moles, of the amount of $M^{2+}$;
  $R^+$ represents a monovalent ion of a metal chosen from sodium, potassium and silver, or a mixture of such ions, the sodium and potassium ions then preferably representing, alone or together, at least 90%, in moles, of the amount of $R^+$;
  the material comprises, preferably in an amount by weight of less than or equal to 10% of the weight of the material, as doping agent, an element chosen from copper, iron, manganese, zinc and lithium, or a mixture of such elements.

For applications as luminescent material, for example for medical imaging applications, the material according to the invention can meet one, preferably several and even all, of the characteristics below:
  $M^{2+}$ represents a divalent ion of a metal chosen from calcium, magnesium and strontium, or a mixture of such ions;
  $R^+$ represents a monovalent ion of a metal chosen from sodium, potassium and silver, or a mixture of such ions;
  the material comprises, preferably in an amount by weight of less than or equal to 10% of the weight of the material, as doping agent, an element chosen from copper, iron, manganese, zinc, lanthanum, cerium, praseodymium, promethium, samarium, europium, gadolinium, terbium, dysprosium, erbium, thulium, neodymium and ytterbium, or a mixture of such elements.

For applications as conductive material, for example in the field of batteries, the material according to the invention can meet one, preferably several, and even all, of the characteristics below:

$M^{2+}$ represents a divalent ion of a metal chosen from magnesium, nickel, zinc, cobalt and copper, or a mixture of such ions;

$R^+$ represents a monovalent ion of a metal chosen from sodium, potassium and lithium, or a mixture of such ions;

the material comprises, preferably in an amount by weight of less than or equal to 10% of the weight of the material, as doping agent, an element chosen from iron and chromium, or a mixture of such elements.

In vitreous form, the material according to the invention can be of porous type. The size of its pores can then vary from a nanometer to a millimeter, that is to say between 1 nm and 1 mm. Its porosity can just as well be interconnected as non-interconnected. It can represent up to 95% by volume of the total volume of the material.

The material according to the invention can consist of a hybrid material, that is to say a material additionally containing one or more organic, bioorganic or bioinorganic molecules, functions or polymers. Mention may be made, as examples of such polymers or molecules, of polycaprolactone, polyvinyl alcohol, poly(lactic-co-glycolic acid), gelatin and chitosan, the pentapeptide osteostatin, bone morphogenetic proteins (BMPs), and the like, such a list being in no way limiting of the invention.

The material according to the invention can also consist of a composite material, in which organic nano- or microdomains are included in the inorganic part, or vice versa.

Specific materials according to the invention meet one or more of the following characteristics:

$M^{2+}$ represents a divalent ion: calcium, magnesium or strontium, $R^+$ represents a monovalent ion: potassium, sodium or lithium.

Specific materials in accordance with the present invention correspond to the general formulae (Ia) to (Ig) below:

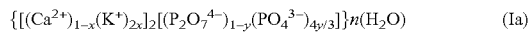 (Ia)

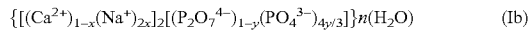 (Ib)

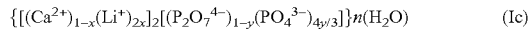 (Ic)

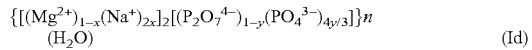 (Id)

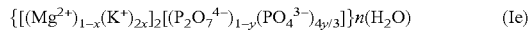 (Ie)

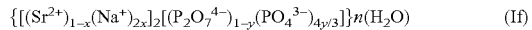 (If)

 (Ig)

in which x, y and n are as defined above.

In particular, each of these materials can be in the vitreous form, the percentage by weight of water which is contained therein being greater than 0 and less than or equal to 20, preferably between 5 and 20%, limits included.

Each or these materials can meet one or more of the specific characteristics defined above.

According to another aspect, the present invention relates to a process for the preparation of a material according to the invention.

According to the invention, this process advantageously comes under the field of soft chemistry, more particularly of the sol-gel route.

This process comprises:

bringing together appropriate amounts of a solution, in particular of an aqueous solution, of a precursor of a metal M chosen from calcium (Ca), magnesium (Mg), strontium (Sr), copper (Cu), zinc (Zn), cobalt (Co), manganese (Mn) and nickel (Ni), and of a solution, in particular an aqueous solution, of a pyrophosphate precursor, so as to form a material of general formula (I) in the form of a hydrated gel of pyrophosphate of said metal M, in which the percentage by weight of water is greater than 20 and less than or equal to 95, optionally, a step of separation of the material, in the form of a hydrated gel of pyrophosphate of the metal M, from the reaction medium, by any method conventional in itself for a person skilled in the art, in particular by centrifugation, filtration, settling, evaporation and the like; and optionally, the heating of the hydrated gel thus formed at a temperature of between 60 and 200° C., preferably of between 40 and 150° C. and preferentially of between 60 and 100° C., for a period of time of between 2 and 168 h, for example of approximately 48 h, so as to be obtain a vitreous material of general formula (I) in which the percentage by weight of water is greater than 0 and less than or equal to 20 and preferably between 5 and 20, limits included.

When, in the general formula (I), $M^{2+}$ represents a mixture of divalent ions of different metals, the first step of the process according to the invention, of bringing together with the solution of a pyrophosphate precursor, can be carried out starting from a solution containing a mixture of precursors, each of one of said metals, and/or containing a precursor of several of said metals.

When, in the general formula (I), x is greater than 0, that is to say when the material contains a nonzero amount of the $R^+$ ion, a precursor of this metal R can be added either to the solution of precursor of the metal M or to the solution of pyrophosphate precursor before the step in which these solutions are brought together.

Likewise, when the material according to the invention contains a doping agent, a precursor of this doping agent can be added either to the solution of precursor of the metal M or to the solution of pyrophosphate precursor, depending on its nature.

The step in which the solutions of precursors are brought together can be followed by a step of washing the counterions with demineralized water. This step can be carried out by employing centrifugation cycles, in particular from 1 to 10 cycles, for example at a speed of between 2000 and 15 000 revolutions per minute, for a period of time of between 30 seconds and 20 minutes. At the end of this washing step, the hydrated gel of oxide of pyrophosphate of the metal M is obtained, in which the percentage by weight of water is greater than 20 and less than or equal to 95.

Contrary to the processes by fusion provided by the prior art for the preparation of glasses consisting of calcium and phosphorus oxides, the process according to the invention does not comprise any step at a temperature of greater than 200° C., with the result that it is associated with reduced processing costs. In addition, it makes it possible to obtain a material with a nonzero degree of hydration and in particular in which the percentage by weight of water is greater than or equal to 5% by weight of water, with respect to the total weight of the material.

It is within the competences of a person skilled in the art to determine, for each of the steps of bringing together the solutions of precursors and of heating the hydrated gel obtained, the operating parameters to be employed in order to obtain the desired degree of hydration of the material. Such a determination can be carried out theoretically or experimentally, by measuring, for each combination of parameters, the degree of hydration obtained, for example by thermogravimetric analysis. For example, for the heating step, it is obvious that, the higher the heating temperature and/or the longer the heating time, the lower the degree of hydration of the final material.

The process according to the invention advantageously makes it possible to control the form of the phosphate entities present in the material and the relative amount of each of these forms. It makes it possible in particular to control the amount of pyrophosphate entities contained in the material and thus to control the rate of dissolution which this material will exhibit in biological fluids. In particular, in the case where the material has the form of an amorphous phase and of a crystalline phase, the process according to the invention also makes it possible to control the amount of each of the phosphate entities in each of these phases.

This process by the sol-gel route in addition exhibits the advantage of making it possible to induce a porosity in the material, furthermore controllably, which in particular proves particularly useful for applications in the field of tissue engineering, and also of making possible good control of the morphology of the material. In addition, it makes it possible to prepare a material in accordance with the invention of hybrid type, that is to say comprising organic functions.

In specific embodiments of the invention, the solution of precursor of the metal is gradually added, in particular dropwise, to the aqueous solution of precursor of the pyrophosphate. This can, for example, be carried out with a flow rate of between 2 and 20 ml/min, for a period of time varying from 1 minute to 5 hours. At the end of this gradual introduction, the hydrated gel according to the invention has formed in the reaction medium.

According to specific embodiments, the process according to the invention additionally meets the following characteristics, implemented separately or in each of their technically effective combinations.

For each of the precursors, respectively of the metal and of the pyrophosphate, the counterion is chosen according to the final biological, physical and/or chemical properties desired for the material.

In specific embodiments of the invention, the precursor of the metal chosen from calcium, magnesium, strontium, copper, zinc, cobalt, manganese and nickel is a salt, for example a chloride, or a nitrate of this metal. It can otherwise be an alkoxide of said metal.

In specific embodiments of the invention, the pyrophosphate precursor is a pyrophosphate associated with four atoms of an element chosen from potassium (K), lithium (Li), sodium (Na) and silver (Ag) or combined with two hydrogen atoms and with one atom of a divalent ion of an alkaline earth metal.

In particular, the pyrophosphate precursor can be potassium pyrophosphate ($K_4P_2O_7$) or sodium pyrophosphate ($Na_4P_2O_7$).

Otherwise, the pyrophosphate precursor can be a pyrophosphate alkoxide.

The concentration of each of the precursors in the solution which contains it depends on the metal under consideration and on the composition desired for the final material.

By way of example, the process according to the invention can comprise a step in which the solution of pyrophosphate precursor is brought together with a solution containing calcium chloride ($CaCl_2$) at a concentration of between 0.180 and 0.730 mol/l.

As regards the solution of pyrophosphate precursor, the concentration of pyrophosphate salt in this solution can, for example, be approximately equal to 0.08 mol/l.

For the implementation of the process according to the invention, there are, for example, employed initial amounts of 0.004 mol of $CaCl_2$ and 0.017 mol of pyrophosphate salt.

More generally, the initial $M/(P_2O_{07})$ molar ratio is preferably between 0.2 and 0.9.

The material according to the invention has applications in several fields, in its vitreous form and/or in its hydrated gel form.

In particular, according to one of its aspects, the present invention relates to the use of a material according to the invention in the manufacture of bone substitutes or of prostheses coatings, for bone repair and/or reconstruction, in particular, but nonlimitingly, for applications in orthopedic and dental surgery.

These bone substitutes and/or prostheses coatings can in particular be of the type capable of delivering active molecules.

The vitreous material according to the invention also has other applications, in particular in the optical field, in the manufacture of ion conductors or the manufacture of electrolytes and batteries, or else in the manufacture of luminescent devices.

BRIEF DESCRIPTION OF THE DRAWINGS

The characteristics and advantages of the invention will become clearly apparent in the light of the examples below, provided simply by way of illustration and without being limiting of the invention, with the support of FIGS. 1-11, in which.

DETAILED DESCRIPTION OF THE EMBODIMENTS

Example 1—Preparation of Vitreous Materials in Accordance with the Invention Vitreous materials in accordance with the invention, respectively called Material A and Material B, are prepared, which materials have the following compositions:

Material A:

$\{[(Ca^{2+})_{0.84}(K^+)_{0.33}]_2[(P_2O_7^{4-})_{0.80}(PO_4^{3-})_{0.27}]\} \cdot 0.43H_2O$ Material B:

$\{[(Ca^{2+})_{0.80}(K^+)_{0.40}]_2[(P_2O_7^{4-})_{0.80}(PO_4^{3-})_{0.27}]\} \cdot 0.37H_2O$.

Material A is a glass, whereas Material B is a glass-ceramic.

These materials are each prepared by a process in accordance with the present invention, in the following way.

Step 1

A solution (1) of calcium precursor is prepared by dissolving $CaCl_2$ in 20 ml of distilled water, in a proportion of 0.4 g for Material A and 1.6 g for Material B.

A solution (2) of pyrophosphate precursor is prepared by dissolving 5.5 g of $K_4P_2O_7$ in 200 ml of distilled water.

Step 2

The solution (1) is added dropwise to the solution (2) over a period of time of 5 min.

Step 3

The resulting solution is washed with demineralized water and subjected to centrifugation for 5 min at 7500 revolutions per minute, in order to obtain a hydrated gel in accordance with the invention.

Step 4

This gel is poured into a container and then treated at a temperature of 70° C. for 48 h, so as to obtain, respectively, the vitreous materials Material A and Material B.

Example 2—Characterization of the Materials

For each of the Materials A and B obtained in example 1, the following characterization experiments were carried out.

Photography

Figure 1:
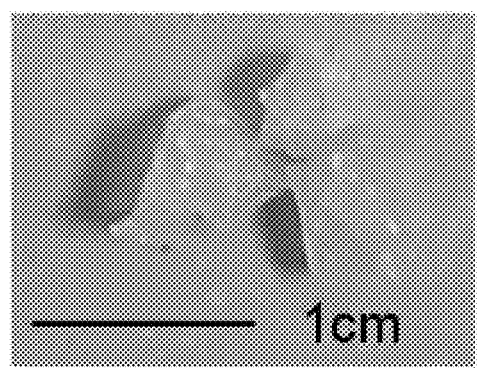
FIG. 1 shows a photograph, with a magnification of ×3.2, of a vitreous material in accordance with the invention with the composition $\{[(Ca^{2+})_{0.84}(K^+)_{0.33}]_2[(P_2O_7^{4-})_{0.80}(PO_4^{3-})_{0.27}]\}.0.43H_2O$.

A photograph of the Material A obtained is shown in FIG. 1.

It is observed therein that this material exists in the form of transparent millimetric pieces, which are characteristic of a glass.

Analysis by ICP-AES Spectrometry (Inductively Coupled Plasma-Atomic Energy Spectroscopy)

For the implementation of this technique, 100 mg of sample, mixed with 500 mg of lithium metaborate $LiBO_2$, were heated at 1100° C. The resulting solid was dissolved in 200 ml of nitric acid at 1 mol/l. The solution was nebulized in the spectrometer (Ultima Horiba device). This technique made it possible to determine the calcium, phosphorus and potassium concentrations of each of the Materials A and B, and thus to confirm their composition and their chemical formulae.

The Ca, P and K concentrations thus determined are shown in table 1 below.

TABLE 1

Ca, K and P concentrations for Materials A and B in accordance with the invention, determined by ICP-AES

| Material | A | B |
|---|---|---|
| [Ca] (mol/l) | 0.61 | 0.54 |
| [K] (mol/l) | 0.16 | 0.27 |
| [P] (mol/l) | 0.66 | 0.63 |

Thermogravimetric Analysis

This analysis was carried out using a Setaram Instrumentation Setsys Evolution device. The measurements were carried out from 25° C. to 900° C., with a gradient of 5° C./min.

The thermogravimetric analysis made it possible to confirm the amount of water in Materials A and B and thus their chemical formulae.

Figure 2:
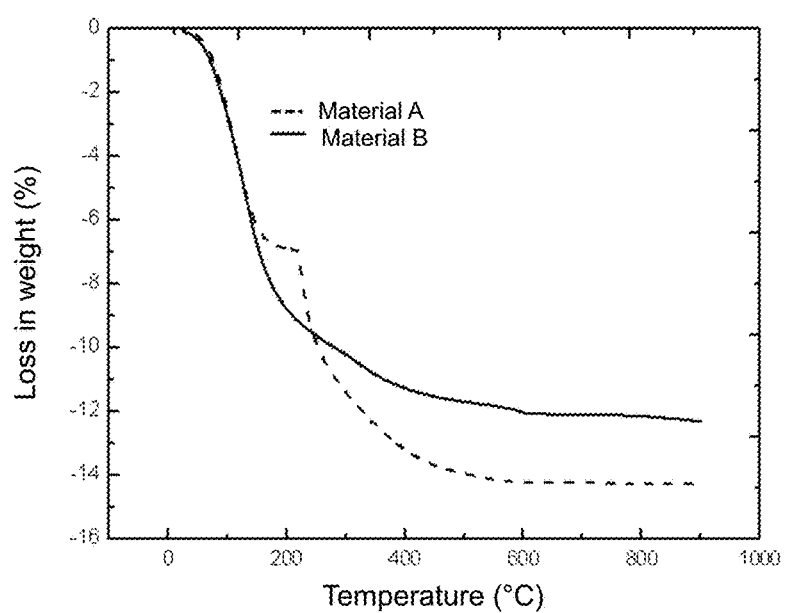
FIG. 2 shows the thermogravimetric analysis curves of vitreous materials in accordance with the invention, the Material A being a glass with the composition $\{[(Ca^{2+})_{0.84}(K^+)_{0.33}]_2[(P_2O_7^{4-})_{0.80}(PO_4^{3-})_{0.27}]\}$. $0.43H_2O$, and the Material B for its part being a glass-ceramic with the composition $\{[(Ca^{2+})_{0.80}(K^+)_{0.40}]_2[(P_2O_7^{4-})_{0.80}$ 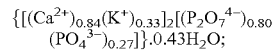 $(PO_4^{3-})_{0.27}]\}.0.3H_2O$.

From the thermogravimetric analysis curves shown in FIG. 2, it was possible to establish a water loss of 14.3% for Material A and of 12.3% for Material B.

X-Ray Diffraction

This analysis was carried out using an Inel CPS 120 instrument, at a wavelength of cobalt $\lambda(K\alpha 1)=1.78897$ Å, from 3 to 110° with a step of 0.02°.

Figure 3:
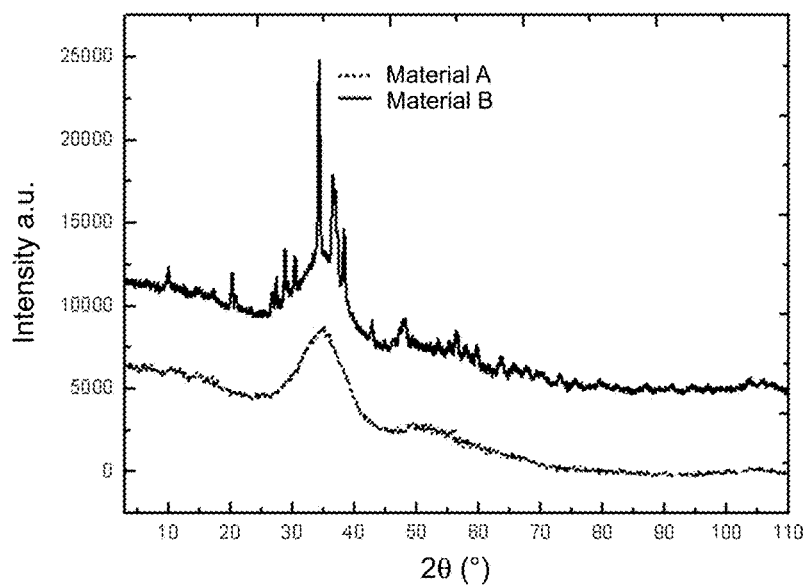
FIG. 3 shows X-ray diffractograms obtained for the vitreous materials Material A and Material B of FIG. 2.

The diffractograms obtained have made it possible to demonstrate the amorphous nature of Material A, having a K/P atomic ratio of less than 0.3, as shown in FIG. 3. In this figure, a halo characteristic of a vitreous material is observed for Material A. For Material B, having a K/P atomic ratio of greater than 0.3, it is indeed observed that the X-ray diffractogram still consists of a halo characteristic of a vitreous material but that peaks have appeared, corresponding to a crystalline phase $(Ca_{10}K_4(P_2O_7)_6 \cdot 9H_2O)$. This combination is typical of a glass-ceramic, formed of a crystalline phase distributed in a vitreous matrix.

Scanning Electron Microscopy

This analysis was carried out using a Leo 435 VP scanning microscope with an acceleration voltage of 15 kV.

Figure 4:
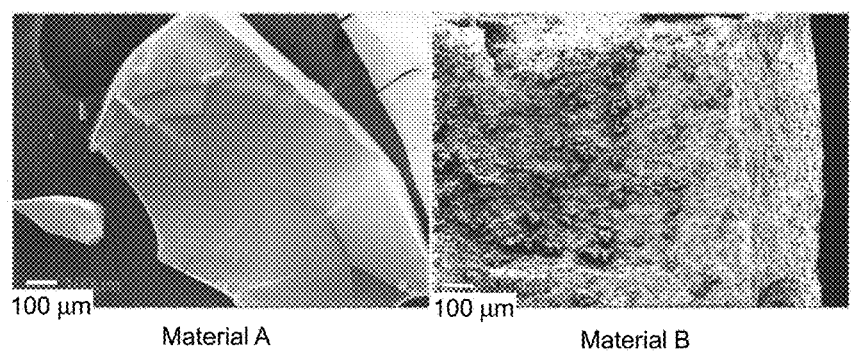
FIG. 4 shows scanning electron microscopy photographs obtained for the vitreous materials Material A and Material B of FIG. 2.

The photographs obtained, for Material A and Material B, are shown in FIG. 4. They demonstrate a morphology typical of a glass for Material A and crystalline entities in a vitreous matrix for Material B, which is characteristic of a glass-ceramic. These results thus confirm those obtained by X-ray diffraction.

Figure 5:
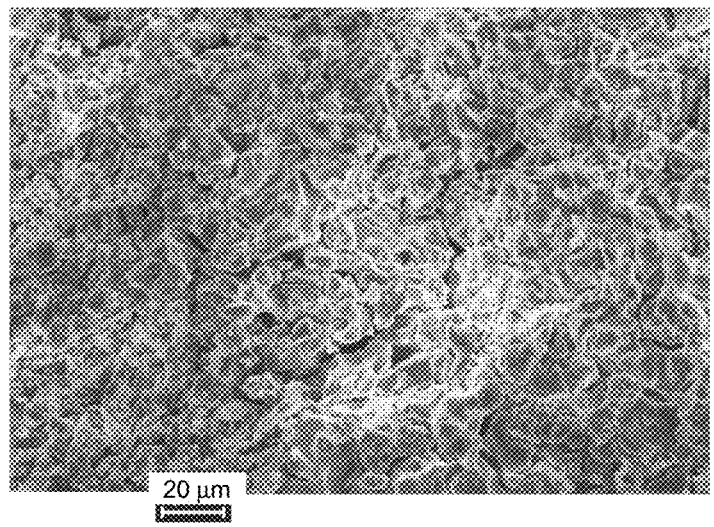
FIG. 5 shows a scanning electron microscopy photograph obtained for the vitreous material Material B of FIG. 2, with a greater magnification (magnification of 500 times)

Furthermore, a photograph obtained for Material B with a greater magnification is presented in FIG. 5. This photograph clearly shows the porosity of this material.

Solid-State Nuclear Magnetic Resonance (NMR)

This analysis was carried out using a 600 MHz NMR spectrometer, 20 kHz MAS, 3.2 mm MAS probe, 0° C. reg $^{31}P$ one pulse; DS=4, NS=4, 45° pulse, recycling time 90 s.

Figure 6:
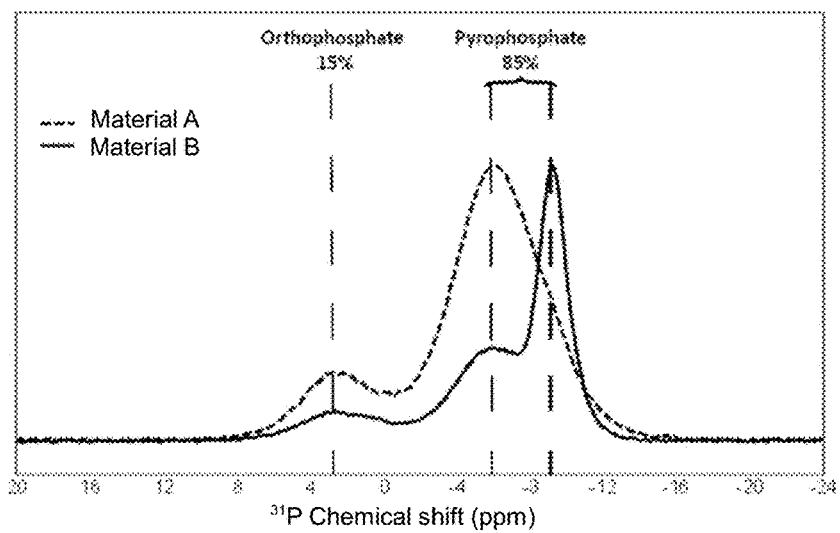
FIG. 6 shows $^{31}P$ NMR spectra obtained for the vitreous materials Material A and Material B of FIG. 2.

The spectra obtained for each of Material A and Material B are shown in FIG. 6.

It is observed therein that the phosphorus contained in the materials is present therein in two forms: pyrophosphate (major) and orthophosphate (minor), whether this be for the glass material (Material A) or for the glass-ceramic material (Material B). A quantitative evaluation of the two forms of phosphates present has been carried out. The results are shown in FIG. 6 (orthophosphate/pyrophosphate distribution: 15%/85%).

Raman Microspectroscopy

This analysis was carried out using a LabRam HR800 confocal microspectrometer (Horiba Jobin Yvon), AR-diode laser/wavelength λ=532 nm.

Figure 7:
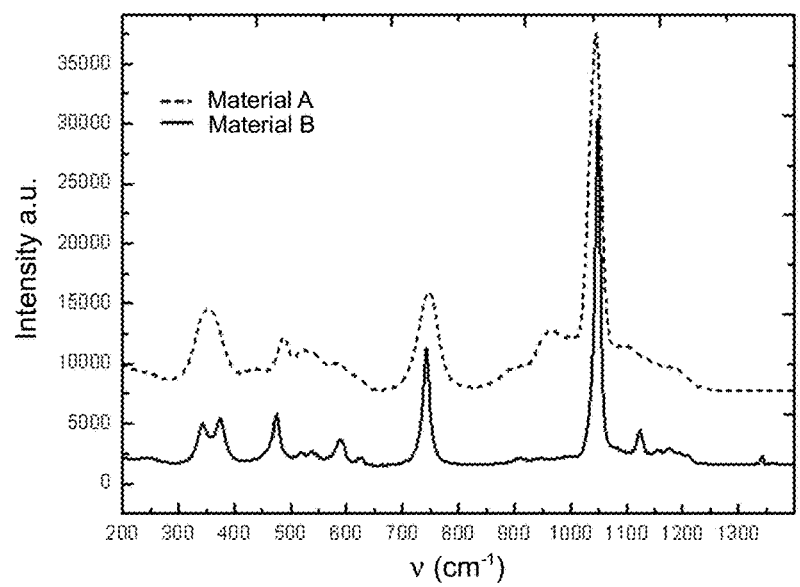
FIG. 7 shows Raman microspectroscopy spectra obtained for the vitreous materials Material A and Material B of FIG. 2.

The spectra obtained are shown in FIG. 7. They confirm, in particular by the presence of the band at 740 cm$^{-1}$, which is a characteristic of the P-O-P vibration, the presence in the materials of phosphorus in the pyrophosphate entity form, this being the case both for Material A and for Material B.

Furthermore, Material A exhibits bands characteristic of orthophosphates, in particular the band at 963 cm$^{-1}$, which are more intense than for Material B, which is consistent with the quantitative analyses obtained by solid-state NMR, shown in FIG. 6 (orthophosphate/pyrophosphate distribution 15%/85%).

Example 3—Study of the Dissolution in a Solution Simulating Blood Plasma

The kinetics of dissolution of Material A were studied in a solution simulating blood plasma (SBF, simulated body fluid). SBF has an ion composition similar to that of human blood plasma (Kokubo et al., 1990, *J. Biomed. Mater. Res.*, 24, 721-734).

The dissolution test was carried out by immersion of samples of Material A in the solution of simulated body fluid SBF. The principle of the use of this solution is to demonstrate the bioactivity of the material, characterized by its dissolution in the solution, followed by the formation of a precipitate, such as hydroxyapatite, at the surface of the material. The operating protocol is as described in the standard ISO 23317:2007.

More specifically, for each sample, 100 mg of Material A were immersed at 37° C. in 50 ml of SBF. At regular time intervals, a sample was withdrawn and analyzed by ICP-AES, after filtration and ten-fold dilution, for its concentration of calcium and phosphorus.

Figure 8:
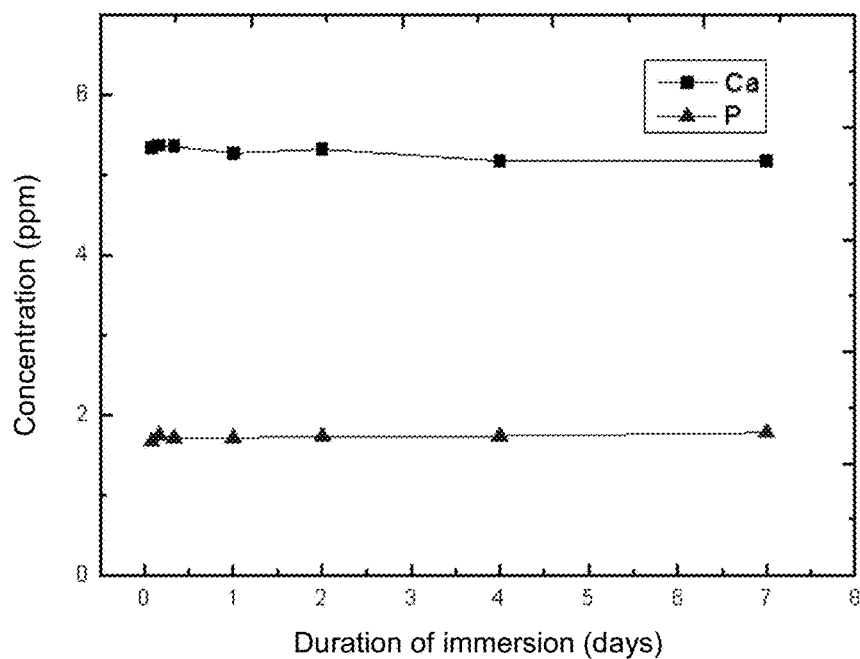
FIG. 8 shows graphs illustrating, for Material A of FIG. 2, the change in the concentrations of calcium and of phosphorus as a function of the duration of immersion of a sample of this material in simulated body fluid (SBF) at 37° C.

The curves illustrating the change in these concentrations as a function of the duration of immersion in SBF are shown in FIG. 8.

A very slight decrease in the calcium concentration and a very slight increase in the phosphorus concentration are observed therein after 7 days of immersion. The amplitude of these variations is only a tenth of a ppm.

In comparison, for a conventional bioactive glass provided by the prior art SiO$_2$—CaO—P$_2$O$_5$ synthesized by the sol-gel route (Sepulveda et al., 2002, *Journal of Biomedical Materials*, 61, 301-311), after immersion of 0.5 g of material in 45 ml of SBF, a strong decrease in the phosphorus concentration and a high increase in the calcium concentration (with amplitudes of several hundred ppm) are observed in only a few hours. These variations reflect a very high dissolution of the material and possibly a precipitation of phases.

Example 4—Cytotoxicity Test

Material A in accordance with the invention, in the powder form, was sterilized by gamma rays, at a dose of 25 KGy, and then subjected to an indirect cytotoxicity test with mesenchymal stem cells, isolated from human bone marrow stroma (HBMSCs).

A culture medium solution was brought together with the material (in a proportion of 100 mg material/ml of medium) for 24 h. After 24 h, a first sample of 100 ml of this solution was withdrawn, supplemented with 10% v/v of fetal calf serum and tested on an HBMSC culture for 24 h (extract (1)).

At the same time, immediately after withdrawal of the first sample, an equivalent volume of fresh medium was added to the solution in order to keep the 100 mg of material/ml of medium ratio constant. After an additional 24 h, a second sample of 100 ml of this solution was withdrawn, supplemented with 10% v/v of fetal calf serum and tested on an HBMSC culture for 24 h (extract (2)).

At the same time, immediately after the withdrawal of a second sample, an equivalent volume of fresh medium was added in order to keep the 100 mg of material/ml of medium ratio constant. After an additional 24 h, a third sample of 100 ml of this solution was withdrawn, supplemented with 10% v/v of fetal calf serum and tested on an HBMSC culture for 24 h (extract (3)).

For each of the extracts, the cell viability and the metabolic activity of the cells were evaluated after culturing for 24 h, respectively using the test with neutral red (NR) and the test with 3-(4,5-dimethylthiazol-2-yl)-2,5-diphenyltetrazolium bromide (MTT) (Parish et al., 1983, *Journal of Immunological Methods*, 58, 225-37).

In accordance with the standard AFNOR 6NFEN30993, it was considered for this experiment that a product is regarded as cytotoxic when the percentage of mortality is greater than 25% (that is to say that the cell viability is less than 75%).

Figure 9:
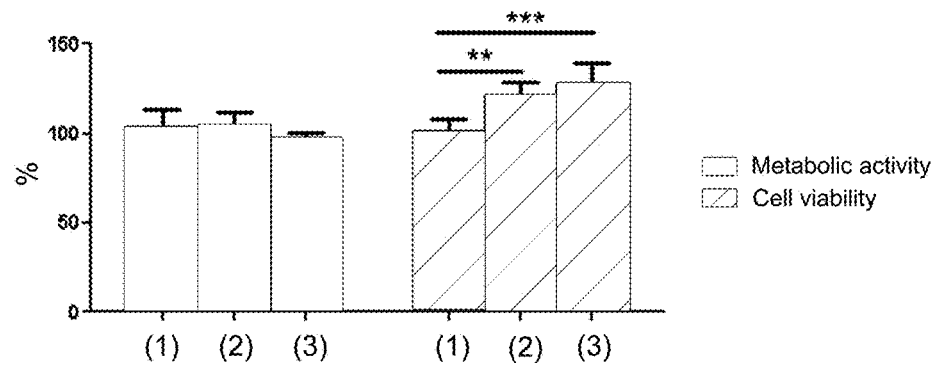
FIG. 9 shows a graph illustrating the cell viability and the metabolic activity of mesenchymal stem cells isolated from human bone marrow stroma, after culturing in a medium which has been brought into contact beforehand with Material A of FIG. 2 for 24 h (1), 48 h (2) and 72 h (3)

The results obtained are shown in FIG. 9.

They demonstrate that the cells are viable and active whatever the extract used. A significant difference is observed relating to the cell viability (NR) between the first extract and the following two. The degree of cell viability of the first extract, although lower, remains very high, greater than 95%. The living cells are in addition active, no significant variation being revealed by the test with MTT.

These cell tests demonstrate the noncytotoxicity of Material A in accordance with the invention.

Example 5—Preparation of a Vitreous Material in Accordance with the Invention

The glass in accordance with the invention, called Material C, is prepared, which material has the following composition:

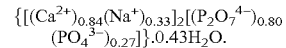

This material is prepared according to the process described in Example 1 above for the preparation of Material A, except that the pyrophosphate precursor used is Na$_2$P$_2$O$_7$.

Figure 10:
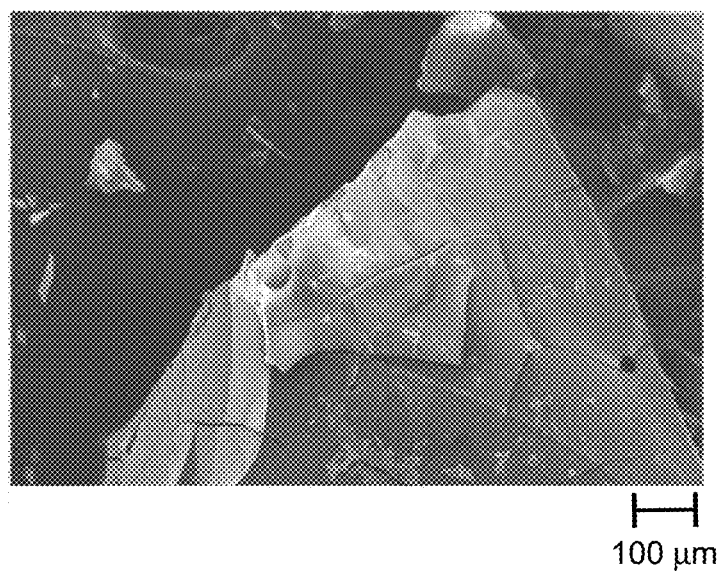
FIG. 10 shows a scanning electron microscopy photograph obtained for a vitreous material in accordance with the invention with the composition $\{[(Ca^{2+})_{0.84}(Na^+)_{0.33}]_2[(P_2O_7^{4-})_{0.80}(PO_4^{3-})_{0.27}]\} \cdot 0.43H_2O$ (Material C)

This material is subjected to analysis by scanning electron microscopy, as described in Example 2 above. The photograph obtained is shown in FIG. 10. A morphology typical of a glass is observed therein.

Figure 11:
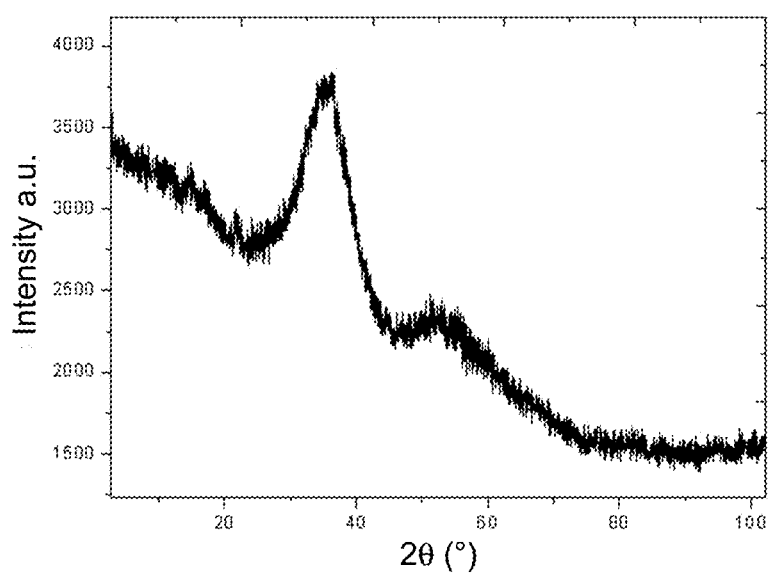
FIG. 11 shows an X-ray diffractogram obtained for the vitreous material of FIG. 10.

An analysis by X-ray diffraction, carried out in accordance with the conditions described in Example 2 above, confirms this observation. The diffractogram obtained, presented in FIG. 11, indeed shows a diffuse halo characteristic of a vitreous material.

The invention claimed is:

1. A material comprising a compound of general formula (I):

wherein:

$0 < x \leq 0.8,$ $0 \leq y \leq 0.8,$ n is a positive rational number such that a percentage by weight of water in the material is greater than 0 and less than or equal to 95, $M^{2+}$ represents a divalent ion of a calcium, and $R^+$ represents a monovalent ion of a sodium.

2. The material as claimed in claim 1, wherein y in the general formula (I) is such that: $0 \leq y \leq 0.5$.

3. The material as claimed in claim 1, wherein n in the general formula (I) is such that the percentage by weight of water in the material is greater than or equal to 5 and less than or equal to 95.

4. The material as claimed in claim 1, wherein n in the general formula (I) is such that the percentage by weight of water in the material is greater than 0 and less than or equal to 20, and wherein the material is an amorphous material.

5. The material as claimed in claim 4, wherein the material is porous.

6. The material as claimed in claim 1, wherein n in the general formula (I) is such that the percentage by weight of water in the material is greater than 20 and less than or equal to 95, and wherein the material is a gel.

7. The material as claimed in claim 1, wherein a $R^+/P$ molar ratio is less than or equal to 0.3.

8. The material as claimed in claim 1, wherein a $R^+/P$ molar ratio is greater than 0.3.

9. The material as claimed in claim 1, doped with a percentage by weight of between 0 and 15%, limits included, of an element selected from the group consisting of copper, iron, chromium, manganese, zinc, lanthanum, lithium, cerium, praseodymium, promethium, samarium, europium, gadolinium, terbium, dysprosium, erbium, thulium, neodymium and ytterbium, and of any mixture of said elements.

10. The material as claimed in claim 1, in a form of monoliths, nanoparticles, microparticles, a thin layer with a thickness of less than 10 μm, a thick layer with a thickness of greater than 10 μm or fibers.

11. A method of manufacturing bone substitutes, said method comprising a step of manufacturing bone substitutes from the material as claimed in claim 1.

12. A method of manufacturing prostheses coatings, said method comprising a step of manufacturing prostheses coatings, from the material as claimed in claim 1.

* * * * *